(12) United States Patent
Duc et al.

(10) Patent No.: US 10,709,444 B2
(45) Date of Patent: Jul. 14, 2020

(54) THREAD INSERTION DEVICES

(71) Applicant: Allergan Industrie SAS, Pringy (FR)

(72) Inventors: Antoine Duc, Saint Jean le Vieux (FR); Bastien Mandaroux, Metz-Tessy (FR)

(73) Assignee: Allergan Industrie SAS, Pringy (FR)

( * ) Notice: Subject to any disclaimer, the term of this patent is extended or adjusted under 35 U.S.C. 154(b) by 93 days.

(21) Appl. No.: 15/414,219

(22) Filed: Jan. 24, 2017

(65) Prior Publication Data
US 2018/0206964 A1    Jul. 26, 2018

(51) Int. Cl.
*A61F 2/00* (2006.01)
*A61B 17/06* (2006.01)
*A61B 17/34* (2006.01)
*A61B 17/00* (2006.01)

(52) U.S. Cl.
CPC ........ *A61B 17/06109* (2013.01); *A61B 17/06* (2013.01); *A61B 17/06066* (2013.01); *A61B 17/3468* (2013.01); *A61B 2017/00792* (2013.01); *A61B 2017/061* (2013.01); *A61F 2/0059* (2013.01)

(58) Field of Classification Search
CPC .......... A61F 2/0059; A61F 2/105; A61F 2/10; A61B 17/3468
See application file for complete search history.

(56) References Cited

U.S. PATENT DOCUMENTS

| | | |
|---|---|---|
| 1,250,114 A | 12/1917 | Bigelow et al. |
| 1,558,037 A | 10/1925 | Morton |
| 1,591,021 A | 7/1926 | Davis |
| 2,092,427 A | 9/1937 | Frederick |
| 2,302,986 A | 11/1942 | Vollrath |
| 2,571,653 A * | 10/1951 | Bastien ............... A61M 5/3243 604/198 |
| 3,204,635 A | 9/1965 | Voss |

(Continued)

FOREIGN PATENT DOCUMENTS

| | | |
|---|---|---|
| EP | 0648474 A1 | 4/1995 |
| EP | 0809968 A1 | 12/1997 |

(Continued)

OTHER PUBLICATIONS

Bleyer, Mark, SIS Facial Implant 510(k) Summary, Cook Biotech, Inc., May 19, 2005.

*Primary Examiner* — Suba Ganesan
*Assistant Examiner* — Aren Patel
(74) *Attorney, Agent, or Firm* — Nathan S. Smith; Danny Mansour; Morgan, Lewis & Bockius LLP

(57) ABSTRACT

Devices and methods for inserting an implant into skin or other tissue of a patient can include a hyaluronic thread coupled with an insertion device that can provide a supportive enclosure for the thread as it is injected into a patient's skin or other tissue. The device can include a cover member, a base, and a thread. The cover member can have a proximal portion, a closed distal portion, and an inner cavity extending from the proximal portion toward the closed distal portion. The thread can be positioned within the inner cavity and extend from the base toward the closed distal portion. The base can be removably coupled to the proximal portion of the cover member. In use, the cover member is insertable into a patient and separable from the base to expose the thread.

21 Claims, 6 Drawing Sheets

(56) References Cited

U.S. PATENT DOCUMENTS

| | | | |
|---|---|---|---|
| 3,674,026 A * | 7/1972 | Werner | A61F 13/26 604/14 |
| 3,910,282 A | 10/1975 | Messer et al. | |
| 4,402,308 A | 9/1983 | Scott | |
| 4,451,253 A | 5/1984 | Harman | |
| 4,820,267 A | 4/1989 | Harman | |
| 4,846,886 A | 7/1989 | Fey et al. | |
| 4,957,744 A | 9/1990 | della Valle et al. | |
| 4,994,028 A * | 2/1991 | Leonard | A61M 37/0069 604/59 |
| 5,116,358 A | 5/1992 | Granger et al. | |
| 5,211,644 A * | 5/1993 | VanBeek | A61B 17/322 604/264 |
| 5,215,535 A * | 6/1993 | Gettig | A61M 5/28 604/198 |
| 5,254,105 A | 10/1993 | Haaga | |
| 5,258,013 A | 11/1993 | Granger et al. | |
| 5,304,119 A | 4/1994 | Balaban | |
| 5,350,385 A * | 9/1994 | Christy | A61B 17/0469 606/139 |
| 5,366,447 A | 11/1994 | Gurley | |
| 5,478,327 A | 12/1995 | McGregor et al. | |
| 5,599,293 A | 2/1997 | Orenga | |
| 5,735,827 A | 4/1998 | Adwers | |
| 5,752,970 A | 5/1998 | Yoon | |
| 5,824,335 A | 10/1998 | Dorigatti et al. | |
| 5,997,513 A * | 12/1999 | Smith | A61M 5/3202 128/919 |
| 6,102,920 A | 8/2000 | Sullivan | |
| 6,159,233 A | 12/2000 | Matsuzawa | |
| 6,162,203 A | 12/2000 | Haaga | |
| 6,214,030 B1 | 4/2001 | Matsutani et al. | |
| 6,450,937 B1 | 9/2002 | Mercereau | |
| 6,547,762 B1 * | 4/2003 | Botich | A61M 25/0631 604/110 |
| 6,936,297 B2 | 8/2005 | Roby et al. | |
| 7,041,088 B2 | 5/2006 | Nawrocki et al. | |
| 7,504,386 B2 | 3/2009 | Pressato et al. | |
| 7,559,952 B2 | 7/2009 | Pinchuk | |
| 7,666,339 B2 | 2/2010 | Chaouk et al. | |
| 7,722,582 B2 | 5/2010 | Lina et al. | |
| 7,998,170 B2 | 8/2011 | Cunningham | |
| 8,177,792 B2 | 5/2012 | Lubock | |
| 8,652,216 B2 * | 2/2014 | Chen | A61B 17/3468 623/23.72 |
| 9,801,688 B2 | 10/2017 | Jones | |
| 2001/0008937 A1 | 7/2001 | Callegaro et al. | |
| 2001/0050084 A1 | 12/2001 | Knudson | |
| 2002/0026039 A1 | 2/2002 | Bellini et al. | |
| 2002/0042564 A1 * | 4/2002 | Cooper | A61B 8/12 600/407 |
| 2003/0023250 A1 | 1/2003 | Watschke | |
| 2003/0097079 A1 | 5/2003 | Garcia | |
| 2003/0109769 A1 | 6/2003 | Lowery | |
| 2004/0192643 A1 | 9/2004 | Pressato et al. | |
| 2005/0033362 A1 | 2/2005 | Grafton | |
| 2005/0075606 A1 | 4/2005 | Botich | |
| 2005/0182446 A1 | 8/2005 | DeSantis | |
| 2006/0041320 A1 | 2/2006 | Matsuda | |
| 2006/0136070 A1 | 6/2006 | Pinchuk | |
| 2008/0119876 A1 | 5/2008 | Price et al. | |
| 2008/0125766 A1 | 5/2008 | Lubock | |
| 2008/0139928 A1 | 6/2008 | Lubock | |
| 2008/0167674 A1 | 7/2008 | Bodduluri et al. | |
| 2009/0131908 A1 | 5/2009 | McKay | |
| 2009/0209804 A1 | 8/2009 | Seller | |
| 2009/0318875 A1 | 12/2009 | Friedman | |
| 2010/0256596 A1 | 10/2010 | Chomas | |
| 2011/0093088 A1 * | 4/2011 | Chen | A61B 17/3468 623/23.72 |
| 2011/0152926 A1 | 6/2011 | Vetrecin | |
| 2011/0263724 A1 | 10/2011 | Gurtner et al. | |
| 2011/0282447 A1 | 11/2011 | Niu | |
| 2012/0108895 A1 | 5/2012 | Neuman | |
| 2012/0215230 A1 | 8/2012 | Lubock et al. | |
| 2012/0245629 A1 | 9/2012 | Gross et al. | |
| 2013/0122068 A1 | 5/2013 | Fermanian et al. | |
| 2013/0211374 A1 | 8/2013 | Hetherington | |
| 2013/0226235 A1 | 8/2013 | Fermanian et al. | |
| 2013/0274222 A1 | 10/2013 | Horne et al. | |
| 2013/0310750 A1 | 11/2013 | Hopman | |
| 2014/0221940 A1 | 8/2014 | Clauson et al. | |
| 2014/0228971 A1 | 8/2014 | Kim | |
| 2015/0209265 A1 | 7/2015 | Horne | |
| 2015/0209523 A1 | 7/2015 | Horne et al. | |
| 2015/0327972 A1 | 11/2015 | Horne et al. | |
| 2016/0007990 A1 * | 1/2016 | Solish | A61B 17/06066 606/224 |
| 2016/0074307 A1 | 3/2016 | Gurtner et al. | |
| 2016/0213813 A1 | 7/2016 | Gurtner et al. | |
| 2017/0049972 A1 * | 2/2017 | Persons | A61M 5/3297 |
| 2017/0156754 A1 | 6/2017 | Valbuena | |
| 2017/0290987 A1 | 10/2017 | Mandaroux et al. | |
| 2018/0206963 A1 | 7/2018 | Duc et al. | |
| 2018/0206965 A1 | 7/2018 | Duc et al. | |
| 2018/0206966 A1 | 7/2018 | Duc et al. | |
| 2018/0206967 A1 | 7/2018 | Duc et al. | |

FOREIGN PATENT DOCUMENTS

| | | |
|---|---|---|
| EP | 2422832 A2 | 2/2012 |
| EP | 2103262 B1 | 2/2013 |
| GB | 2336783 A | 5/2003 |
| WO | 199001349 A1 | 2/1990 |
| WO | 1992013579 A1 | 8/1992 |
| WO | 200100190 A2 | 1/2001 |
| WO | 2004022603 A1 | 3/2004 |
| WO | 2006065837 A2 | 6/2006 |
| WO | 2010028025 A | 3/2010 |
| WO | 2011109129 A1 | 9/2011 |
| WO | 2011109130 A1 | 9/2011 |
| WO | 2012054301 A1 | 4/2012 |
| WO | 2012054311 A1 | 4/2012 |
| WO | 2013055832 A1 | 4/2013 |
| WO | 2013082112 A1 | 6/2013 |
| WO | 2015105269 A1 | 7/2015 |

* cited by examiner

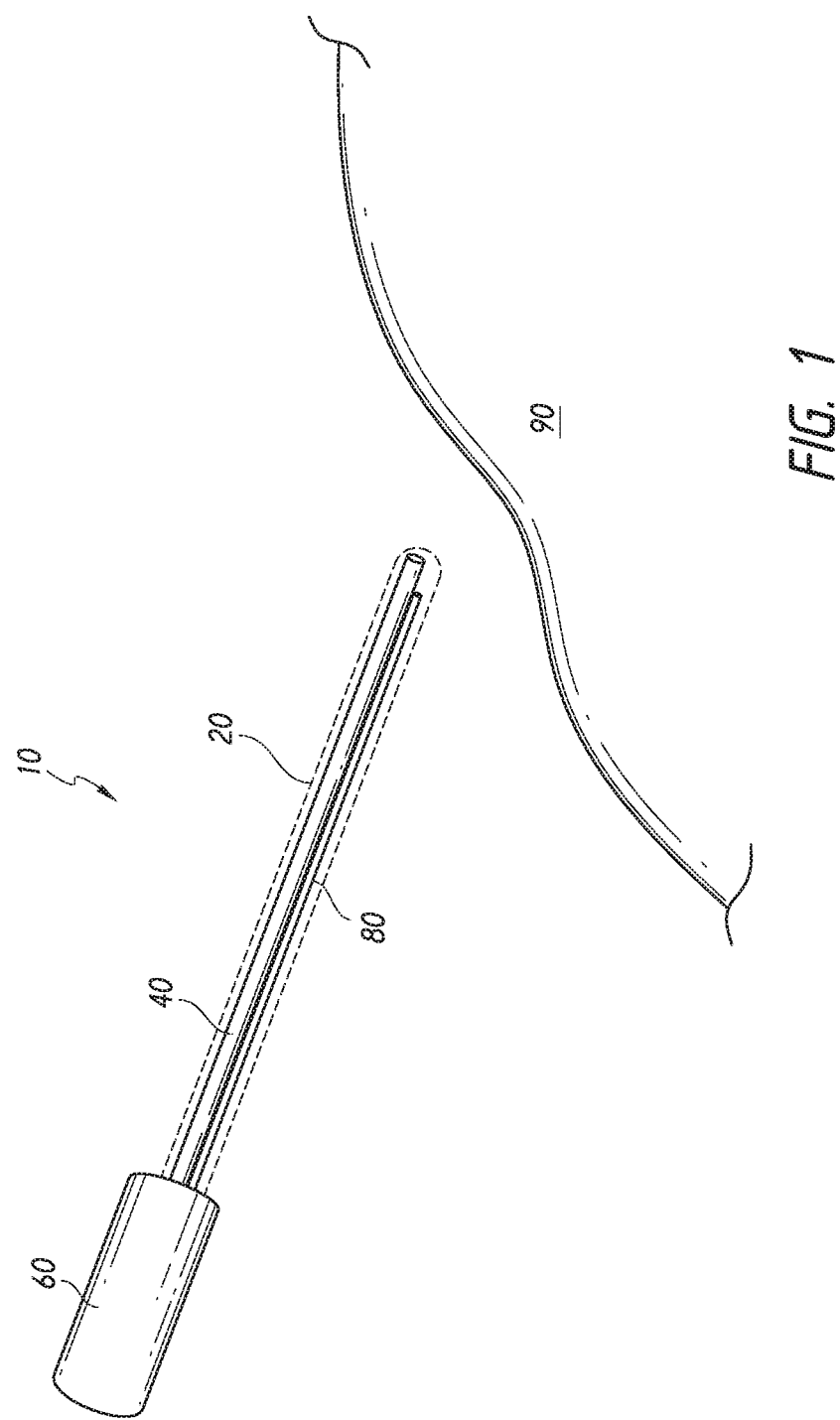

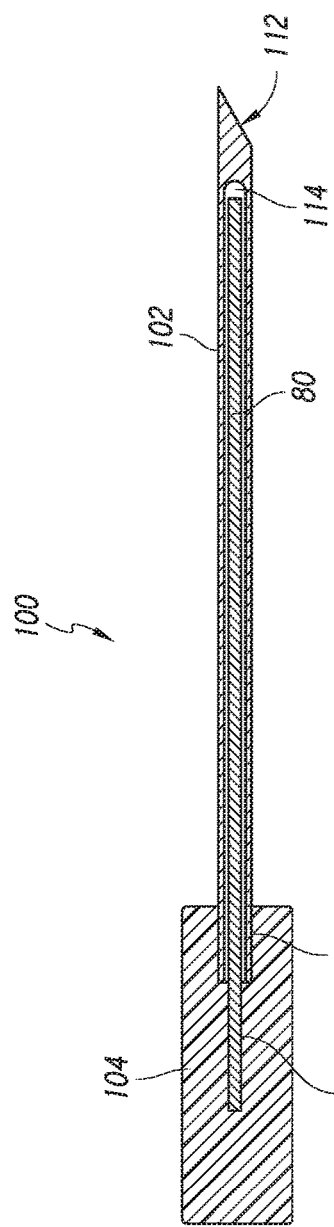
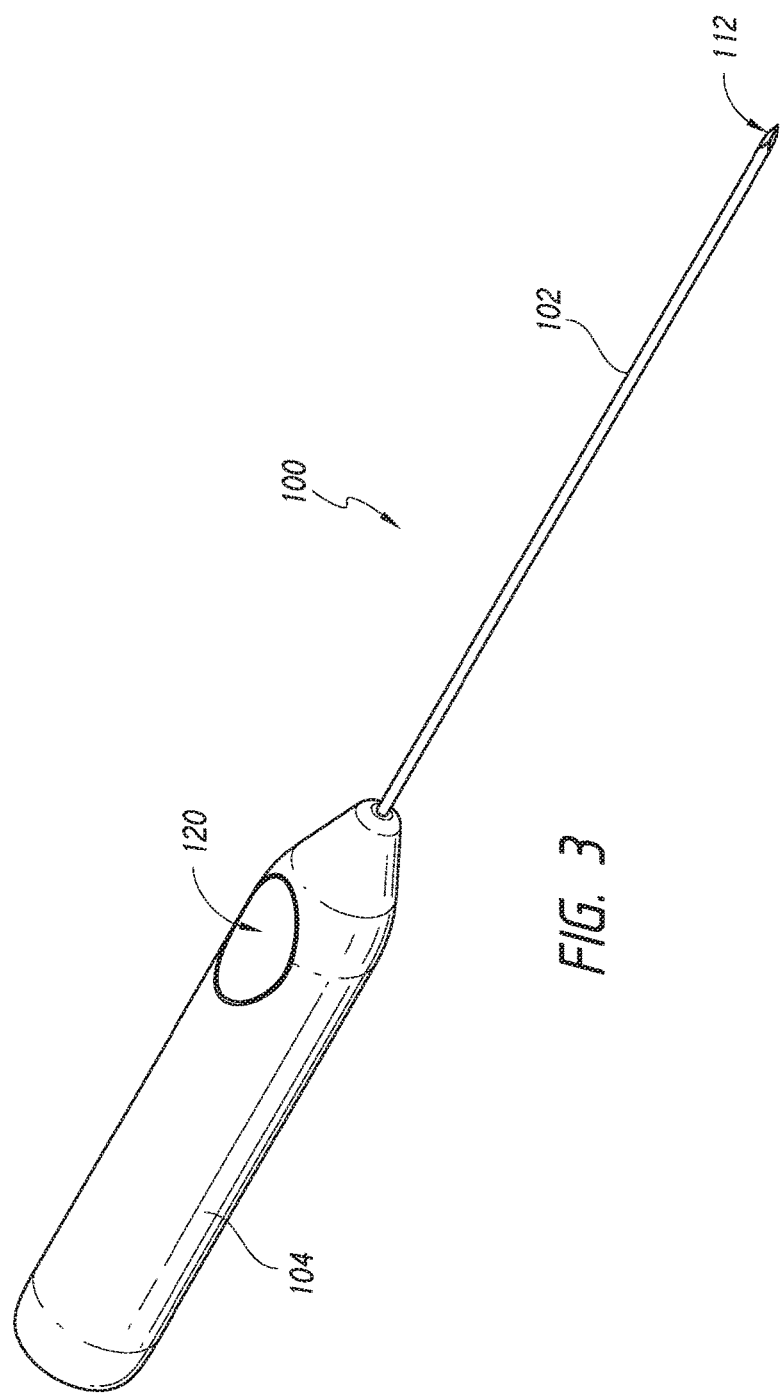

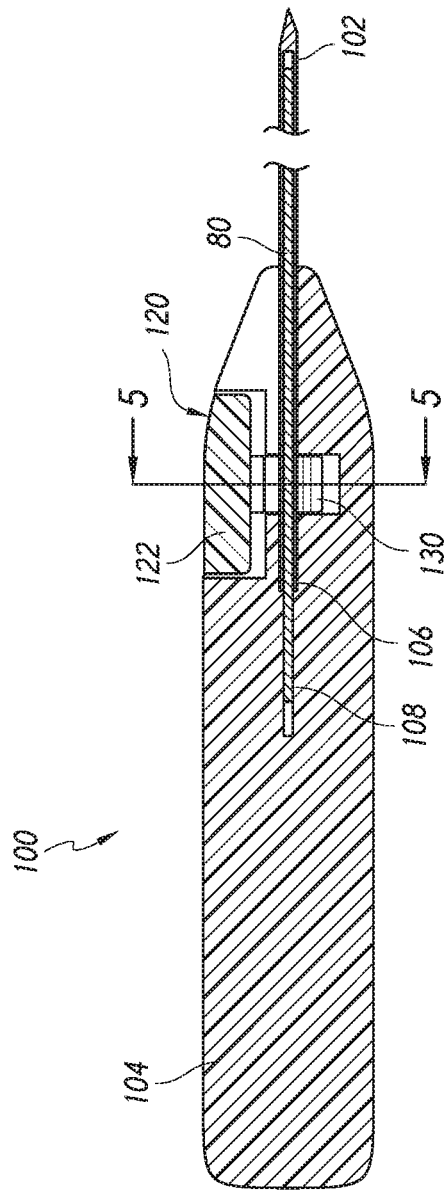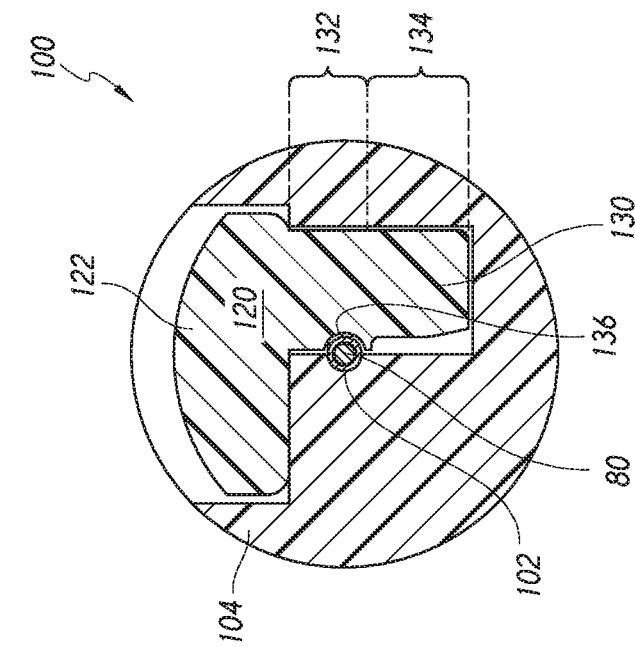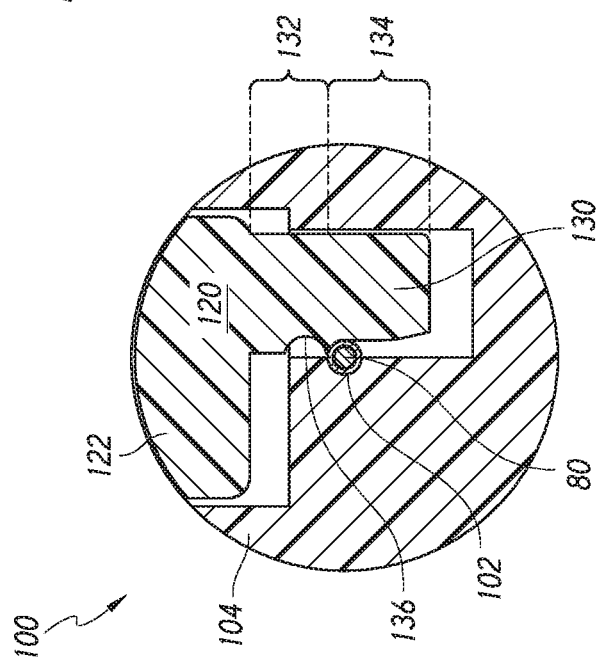

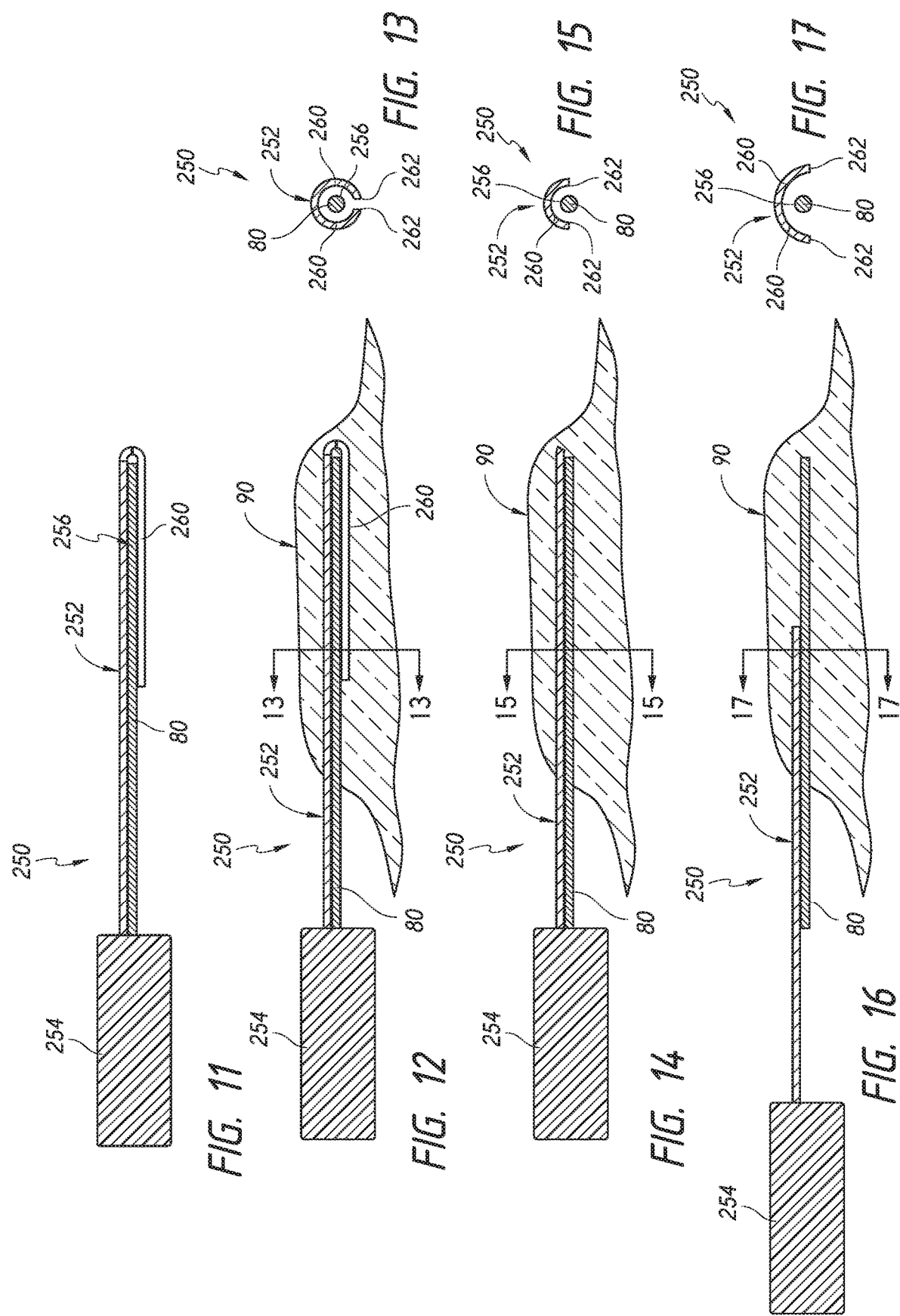

THREAD INSERTION DEVICES

BACKGROUND

Field of the Inventions

The present disclosure relates generally to systems and methods for insertion of an implant, and more particularly, to insertion devices that can comprise a supportive enclosure for an implant, such as a hyaluronic thread, as it is injected into a patient's skin or other tissue.

Background

In recent years, millions of men and women have elected to receive dermal filler injections to rejuvenate aging skin and look younger without surgery or significant downtime. A dermal filler injection is a procedure through which a gel-like, volumizing substance is injected subcutaneously to restore lost volume, add volume to facial features and contours, or smooth fine lines and creases.

Some dermal filler injections are performed using a thread or other implant. Once inserted, the threads used for dermal filler injections can hydrate and expand or swell within the skin of a patient, thereby lessening the appearance of wrinkles, folds, and/or sagging portions of skin.

To insert a thread into the patient, conventional suture procedures can be implemented. For example, using a conventional procedure, a physician couples a thread to a needle and inserts the needle through the skin until achieving a desired placement, which may be adjacent to or under a wrinkle. With the thread placed along or underneath the wrinkle, the needle can be removed and as the thread hydrates, the wrinkle can be "filled" and become less prominent, thus smoothing the skin and achieving a desired aesthetic for the patient.

SUMMARY

The present application discloses various improvements for thread insertion devices and related procedures that can be used to treat humans and/or animals. The devices and procedures can be used, for example, in the context of dermal fillers, surgery (e.g., placing sutures), drug delivery, negative pressure wound therapy, and wound dressing.

In plastic surgery, hyaluronic acid is a common substance used for wrinkle filling. Although hyaluronic acid is typically used as a gel that is injected as a wrinkle filler, some embodiments disclosed herein can utilize hyaluronic acid in a solid form as an implant, e.g., as a hyaluronic acid thread ("HA thread" or "thread").

However, in accordance with some embodiments disclosed herein in the realization that because HA threads are hydrophilic, the mechanical integrity of the thread can rapidly degrade during an implantation procedure. Thread failure can result in improper placement or other complications during the procedure. Thus, a thread that is exposed during insertion of the thread into a patient can become hydrated, causing the thread to swell or expand prematurely and/or lose its tensile strength. If the thread swells within a needle or insertion device, the thread will become lodged within the needle and unable to move relative to the insertion device. The thread can therefore block the needle lumen, prevent separation of the thread from the insertion device, or otherwise complicate the thread placement procedure. In some instances, the swelling of a thread may cause it to engage with skin tissue before the thread has reached a desired position subcutaneously. Thus, the thread becomes immovable during insertion of the thread into the patient. Further, during insertion, friction between the thread and the tissue may increase beyond a tensile strength of the thread and cause the thread to break and separate from the insertion device.

Further, some embodiments of the present devices and methods also contrast with various conventional thread placement devices that include a needle tip that engages a thread at its midsection and allows the thread to fold backwardly or proximally along a length of the needle. In accordance with some embodiments disclosed herein in the realization that because the thread is divided into two strands that extend along the length of the needle, the injection also results in a double-stranded thread placement in which the two strands will swell in situ. Although this may be acceptable in some applications, these conventional devices and procedures are limited because they have a "minimum expansion size" of twice that of a single thread. Accordingly, some of the embodiments disclosed herein enable a single strand of thread to be placed along a desired position instead of the conventional double-stranded thread placement. Advantageously then, some embodiments allow for a lower "minimum expansion size" that can allow a physician to treat wrinkles that are not otherwise good candidates for treatment using only the conventional devices or methods.

Further, because some embodiments disclosed herein "push" a distal end of the thread through the skin, the physician need only to make a single piercing instead of entry and exit piercings required by conventional devices and methods that use a needle whose proximal end attaches to a distal end of the thread and pulls the thread through the entry and exit piercings.

Therefore, some embodiments of the thread insertion devices and procedures disclosed herein can advantageously minimize the number of piercings through the skin, reduce the risk of thread contamination during the insertion procedure, and/or minimize pain and bruising to the patient. Further, some embodiments of the thread insertion devices and procedures disclosed herein can advantageously avoid breakage of the thread during insertion, facilitate safer and easier insertion of the thread, and/or permit greater control over the thread length and insertion depth.

Although particular embodiments of the present disclosure may be disclosed in the context of an implant comprising a thread, it is contemplated that embodiments can be used with various implants. For example, embodiments can be used with an implant comprising a thread, a series of hinged members, or a tube. Further, embodiments can comprise an implant comprising a rigid material, a flexible material, HA threads material, and a material comprising a state of matter including solid, liquid, or any state there between. The implant can comprise a medication and/or medical fluid that are configured to be released by the implant.

In some embodiments, the thread insertion device can comprise a cover member configured to protect an implant, or portions of a device that will be inserted into a patient. The cover member can prevent contamination or damage to a thread. The cover member can also maintain a shape or alignment of a thread relative to a thread insertion device.

The cover member can comprise a cavity or passage configured for a thread to be positioned therein. For example, the cover member can retain at least a portion or an entirety of the thread within a cavity or passage. Contamination or damage to the thread can be prevented when the thread is positioned within a cavity or passage of the cover member. The cover member can prevent contamination of the thread from exposure to an ambient environment, or from a person touching the thread. Further, damage to the thread can be avoided by preventing inadvertent touching or engagement of the thread. Damage to the thread can also be avoided by preventing exposure of the thread to moisture from the patient's skin or tissue, e.g., dermis, epidermis, and subcutaneous tissue, during insertion of the thread.

In some embodiments, the cover member can permit a thread to be positioned along an outer surface of the cover member. The cover member can permit a thread to be positioned along an inner surface of the cover member. The cover member can also provide support to maintain alignment of the thread during insertion.

In some embodiments, the thread can be retained and/or engaged with the cover member and/or a portion of the thread insertion device. Further, the cover member and/or a portion of the thread insertion device can be used to move a thread relative to the insertion device or separate a thread from the insertion device.

For example, the insertion device can comprise one or more portions that extend along an outer surface and/or within the cover member. The thread insertion device can comprise a moveable member within the cover member. A piston can be positioned within a cavity of the cover member. The piston can cause movement of the thread supported on or coupled with the insertion device. Movement of a portion of the insertion device, e.g., the cover member and/or the piston, can release or separate a thread from the insertion device.

In some embodiments, the thread insertion device can comprise a cover member that can be engaged against a thread to retain the thread with the insertion device. A portion of the cover member can be crimped, or compressed, or adhered to engage a portion of a thread. The thread can be adhered to the cover member. To release a thread from the insertion device, a portion of the cover member engaged against a thread can be moved or expanded, or the thread can be separated from the portion of the cover member.

The cover member can comprise a rigid material, a flexible material, a membrane, and/or a heat-shrinkable sleeve. A portion of the cover member comprising a flexible material can extend along an outer surface of the thread. The thread can be positioned between a portion of the cover member comprising a rigid material, and a portion of the cover member comprising a flexible material. The flexible material can enclose a thread during insertion, and can be separated from the thread to permit release of the thread.

The cover member can comprise a flexible or rigid body. The body can comprise a cross-sectional profile that defines a cavity. A shape of a cross-sectional profile of the cover member can comprise an open perimeter, a closed perimeter, a circle, a square, a rectangle, an L-shape, and/or a U-shape. The cover member can comprise an inner surface cross-sectional profile having portions that are tubular along a length of the cover member.

A portion of the cover member can comprise an opening, e.g., a channel or an aperture, between an inner cavity and an outer surface of the cover member. The cover member can permit a thread to be moved through the opening. A thread can be coupled to the insertion device by a portion of the thread that extends through the opening.

The cover member can comprise a proximal portion and a distal portion. The proximal portion can comprise an opening into a cavity of the cover member. The proximal portion can be coupled to other portions of the thread insertion device. The proximal portion can be releasably coupled to a portion of the insertion device.

A cavity of the cover member can extend toward the distal portion of the cover member. The cavity can extend toward a closed distal portion of the cover member. The distal portion of the cover member can comprise a tip portion. The tip portion can comprise an outer surface that tapers toward a point. A tapered or pointed tip can permit the cover member to pierce the patient's skin or tissue to allow insertion of the cover member and thread. The tip can comprise a point, a bevel, or a multiple-sided cutting point, e.g., a pin, a needle, or a trocar. The tip portion can comprises an outer surface that is rounded or blunt. A round or blunt tip can permit insertion of the cover member through an opening of a patient without piercing or causing damage to the patient.

The insertion device can separate or move a cover member away from a thread, or move a thread away from a cover member. A cover member can be moved to uncover or expose a thread. The insertion device can tear a portion of a cover member. The insertion device can tear a flexible portion of the cover material to expose a thread. The cover member can comprise a dissolvable material that degrades or separates from a thread. The dissolvable material of the cover member can break down or change phase when exposed to a temperature. The dissolvable material can dissolve when exposed to a patient's body temperature.

The cover member can comprise a shape memory material configured to move to expose or release a thread. The cover member can enclose or retain a thread within a portion comprising a shape memory material, and move to expose or release a thread. The shape memory material can be activated or deactivated by heating the cover member. The cover member can be heated by applying electricity to the cover member, e.g., resistive heating, or exposing the cover member to the patient's body heat during insertion of the device into the patient.

A support member of the thread insertion device can maintain alignment of a thread relative to the insertion device and permit positioning of the thread within a patient. A portion of a thread can extend along the support member. The support member and a thread adjacent to the support member can move together. The support member can cover or surround a thread to prevent exposure of the thread to contamination or potential damage. A thread can be engaged against the support member to permit movement of the thread with the insertion device.

The distal portion of a cover member can comprise a tip portion. The tip portion can comprise an outer surface that tapers toward a point. A tapered or pointed tip can permit the cover member to pierce a patient's skin or tissue and allow insertion of a portion of the insertion device and thread. The tip can comprise a point, a bevel, or a multiple-sided cutting point, e.g., a pin, a needle, or a trocar. The tip portion can comprise an outer surface that is rounded or blunt. A round or blunt tip can permit insertion of the support member through an opening of a patient without piercing or causing damage to the patient or to pierce the skin or create such an opening while minimizing damage to the patient.

Additional features and advantages of the subject technology will be set forth in the description below, and in part will be apparent from the description, or may be learned by practice of the subject technology. The advantages of the subject technology will be realized and attained by the structure particularly pointed out in the written description and embodiments hereof as well as the appended drawings.

It is to be understood that both the foregoing general description and the following detailed description are exemplary and explanatory and are intended to provide further explanation of the subject technology.

BRIEF DESCRIPTION OF THE DRAWINGS

Various features of illustrative embodiments of the present disclosure are described below with reference to the drawings. The illustrated embodiments are intended to illustrate, but not to limit, the present disclosure. The drawings contain the following figures:

FIG. 1 is a front view of an insertion device, according to some embodiments.

FIG. 2 is a cross-sectional side view of an insertion device, according to some embodiments.

FIG. 3 is a front perspective view of an insertion device, according to some embodiments.

FIG. 4 is a cross-sectional side view of an insertion device, according to some embodiments.

FIGS. 5 and 6 are detail views of an insertion device, taken along line 5-5 in FIG. 4, according to some embodiments.

FIG. 11 is a cross-sectional side view of an insertion device, according to some embodiments.

FIGS. 12 and 13 illustrate a cross-sectional side view and an end view, respectively, of the insertion device of FIG. 11 in a first position within a patient, according to some embodiments.

FIGS. 14 and 15 illustrate a cross-sectional side view and an end view, respectively, of the insertion device of FIG. 11 in an intermediate position within the patient, according to some embodiments.

FIGS. 16 and 17 illustrate a cross-sectional side view and an end view, respectively, of the insertion device of FIG. 11 in a final, retracting position within the patient, according to some embodiments.

DETAILED DESCRIPTION

Figure 7:
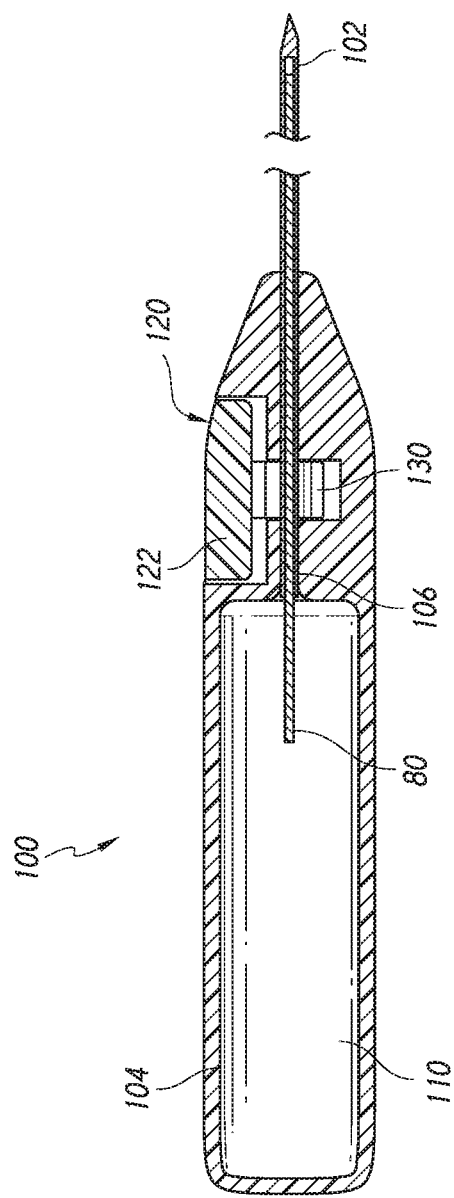
FIG. 7 is a cross-sectional side view of an insertion device, according to some embodiments.

In the following detailed description, numerous specific details are set forth to provide a full understanding of the subject technology. It should be understood that the subject technology may be practiced without some of these specific details. In other instances, well-known structures and techniques have not been shown in detail so as not to obscure the subject technology.

Further, while the present description sets forth specific details of various embodiments, it will be appreciated that the description is illustrative only and should not be construed in any way as limiting. Additionally, it is contemplated that although particular embodiments of the present disclosure may be disclosed or shown in the context of HA thread insertion devices, such embodiments can be used with various devices and implants. Furthermore, various applications of such embodiments and modifications thereto, which may occur to those who are skilled in the art, are also encompassed by the general concepts described herein.

The present application addresses several operational challenges encountered in prior HA thread insertion devices and related procedures. This application provides numerous improvements that enable the physician to control the device more easily, thereby allowing precise positioning of the implant while minimizing trauma to the patient.

For example, in accordance with some embodiments, the present application discloses various features and advantages of thread insertion devices and procedures that can be used to deliver an implant into skin or other tissue of a patient. The thread insertion device can avoid contamination a HA thread and protect the thread's mechanical properties during insertion. The thread insertion device can also permit a physician to precisely position the implant while minimizing trauma to the patient. The present disclosure, along with co-pending U.S. patent application Ser. Nos. 15/414,195, 15/414,248, 15/414,278, and 15/414,306, each filed on the same day as the present application, includes various features that can be interchangeably implemented into embodiments of thread insertion devices and methods of their use and the contents of these applications are incorporated herein in by reference in their entireties. For example, various aspects of the engagement mechanisms, actuation components, cover members, handles, and other features for delivering, protecting, engaging, advancing, or otherwise handling a needle and/or thread, can be combined or substituted with features of embodiments disclosed herein.

Further, some embodiments of the thread insertion devices and procedures disclosed herein can advantageously allow a single strand of HA thread to be positioned in situ as opposed to conventional double-stranded thread placement. Some embodiments disclosed herein relate to enclosure-type thread insertion devices.

Referring to the figures, a schematic illustration of a general embodiment of a thread insertion device 10 is shown in FIG. 1. The insertion device 10 can comprise a cover member 20, a support member 40, and a base 60. A HA thread 80 can be positioned between the cover member 20 and the support member 40 (each of the embodiments discussed herein refers to the HA thread 80, but the HA thread 80 can be substituted, modified, or replaced in any of the embodiments with a thread or suture having a different type, length, and/or size).

The insertion device 10 comprises a proximal portion and a distal portion. The proximal portion comprises the base 60, and the distal portion comprises the cover member 20 and the support member 40. The base 60 can comprise one or more portions. The base 60 can comprise a first portion and a second portion that is movable relative to the first base portion. The base 60 can comprise a movable member, e.g., a button or engagement member, to permit a portion of the insertion device to be separated from the base 60.

The support member 40 can be coupled to the base 60 and extend from the base 60 toward the distal portion of the insertion device 10. The support member 40 can comprise a shaft, a rod, and/or a plate having a longitudinal length. A cross-section, transverse to the longitudinal length of the support member 40, can be non-tubular and/or tubular, and can comprise a shape or profile such as a circle, a square, a rectangle, an L-shape, and/or a U-shape.

The cover member 20, illustrated in broken lines, can extend around the outer surface of the support member 40. The cover member 20 can be coupled to the base 60. The cover member 20 can comprise a rigid material, a flexible material, or any combination thereof. In some embodiments, the cover member 20 can comprise any of a rigid material, such as stainless steel (e.g., 304 or grade 316L), titanium, an alloy of nickel and titanium (e.g., nitinol), and a synthetic fluoropolymer of tetrafluoroethylene such as Polytetrafluoroethylene (PTFE). The cover member 20 can have a bending stiffness or rigidity that is greater than a bending stiffness or rigidity than the thread 80. As such, the cover member 20 can provide a longitudinal support and protection to reduce or eliminate bending, breakage, and/or contamination of the thread 80 during handling, delivery, and the procedure itself.

Additionally, in some embodiments, the insertion device can comprise a single moveable member that can function to provide both a covering and a support for the thread. Thus, the moveable member can combine the cover member and the support member features into a single component.

A thread 80 can be positioned between the support member 40 and the cover member 20. The thread 80 can extend along a longitudinal length of the support member 40. The cover member 20 can prevent contamination or damage to the thread 80.

In accordance with some embodiments, a physician can hold the insertion device 10 by the base 60, and the distal portion of the device directed through the skin 90 of a patient so that a portion of the device and thread are positioned under the skin 90. The physician can advance the support member 40 and the cover member 20 into the skin 90 of the patient by piercing the skin 90 using a sharp portion of the support member 40 and/or the cover member 20. In some methods, the skin 90 of the patient can be pierced or cut open before directing the insertion device 10 into the patient.

Once the skin 90 has been pierced and the support member 40 and the thread 80 are positioned subcutaneously, the cover member 20 can be removed from the device 10. For example, the cover member 20 can be removed from the distal portion of the insertion device 10 before or after engaging the insertion device 10 against the skin 90. In some embodiments, the insertion device 10 can be configured so that the cover member 20 is removed from the distal portion as the insertion device 10 is inserted into the skin 90. Further, in some embodiments, the insertion device 10 can also or alternatively be configured so that the cover member 20 is inserted into the skin 90 and then removed. For example, the insertion device 10 can be configured so that a portion of the device, e.g., the cover member 20, is inserted through a first portion of the skin 90 and removed through a second portion of the skin 90. Additionally, in some embodiments, the cover member 20 can be left in situ after implantation and be partially or fully dissolvable within the skin 90.

Referring now to FIGS. 2-10, an embodiment of an insertion device 100 is shown that can comprise a removable cover member 102 and a base 104 that collectively support and protect a HA thread 80. The cover member 102 of the insertion device 100 can be inserted into a patient and then separated from the base to expose the thread 80.

The cover member 102 comprises a proximal portion and a distal portion. The proximal portion of the cover member 102 is configured to engage with the base 104, as illustrated in FIG. 2. The cover member 102 comprises a longitudinal axis that extends along the proximal and distal portions. A cross-sectional profile transverse to the longitudinal axis of the cover can comprise an outer surface that forms a round, oval, square, or rectangle shape. The distal portion of the cover member 102 can comprise a tapered outer surface. The tapered outer surface can comprise a bevel 112, as illustrated in FIG. 2, or multiple bevels, e.g., a trocar, as illustrated in FIG. 3.

The cover member 102 can comprise an inner cavity 114 that extends from the proximal portion toward the distal portion of the cover member 102. The cavity 114 is configured to permit a thread to be positioned within the cavity so that a portion of the thread extends along a longitudinal length of the cavity. An inner surface of the cover member 102 that forms the cavity 114 can have a cross-sectional width that is equal to or greater than a cross-sectional width of the thread 80.

The cover member 102 can have any shape configured to enclose a portion of a thread, including a tubular shape, cylindrical shape, an L-shape, and/or a U-shape. The cover member 102 can have a closed distal portion that encloses an inner cavity. The cover member 102 can be a hypodermic tube. An outer surface of the cover member 102 can comprise a tapering outer surface to permit the cover member 102 to pierce a patient's skin. The cover member can comprise a material that is less flexible than the thread 80 to permit the thread 80 to be directed into a patient without bending or moving the thread 80. For example, in some embodiments, the cover member can comprise a rigid material, such as stainless steel, titanium, and/or an alloy (e.g., an alloy of nickel and titanium, such as nitinol). Each of such materials, along with the structure of the cover member can provide greater column strength than a thread or implant used with the device 100. For example, the cover member 20 can comprise a rigid tubular member or enclosure that comprises a beveled tip, as shown in FIG. 2.

In accordance with some embodiments, the cover member 102 can be removably coupled to the base 104. The base 104 comprises a proximal portion and a distal portion. The distal portion of the base 104 can comprise a cavity having an opening that can be coupled to the cover member and the thread 80. A first portion 106 of the cavity can receive a proximal portion of the cover member 102. The cover member 102 can be separated from the base 104. An inner surface of the base 104 that forms a first portion of the cavity can have a cross-sectional width that can be equal to or greater than an outer surface of the cover member 102. The base 104 and cover member 102 can be coupled by a friction fit between outer surface of the cover member 102 and an inner surface of the base 104.

The cavity of the base 104 can comprise a second portion 108 that extends from the first portion toward the proximal portion of the base 104. An inner surface of the base 104 that forms the second portion of the cavity can have a cross-sectional width that is equal to or greater than an outer surface of the thread 80. The second portion 108 of the cavity can receive a portion of the thread 80. The base 104 can be formed around a proximal portion of the thread 80. A portion of the thread 80, such as the proximal portion, can be coupled to or separated from and moveable relative to the base 104. For example, in some embodiments, a portion of the thread 80 can be adhered to the base 104.

However, although the base 104 and the thread 80 can be coupled together, some embodiments can provide advantages by permitting the thread 80 to be free from the base 104. For example, when the cover member 102 is placed under the skin, the base 104 can be removed first without proximally withdrawing the thread 80 (i.e., the thread 80 remains in place in the cover member 102), and subsequently, the cover member 102 or needle can be removed by the exit point while holding the thread 80. Thus, the thread 80 can be retained in a desired subcutaneous position when the base 104 and the cover member 102 are removed.

Referring to FIG. 3, a cavity 114 is formed between the cover member 102 and the base 104 when the proximal portion of the cover member 102 is coupled to the base 104. The cavity 114 can be configured to enclose and protect a thread 80 from contamination and damage. The thread 80, comprising a proximal portion and a distal portion, can be coupled to the insertion device 100. The thread 80 can be coupled to the insertion device 100 so that a proximal portion of the thread 80 is coupled to the base 104 and the distal portion of the thread 80 is within the cavity 114 of the cover member 102. The distal portion of the thread 80 can extend from the base 104 toward the distal portion of the cover member 102.

As noted herein, one of the advantages of some embodiments is that the cover member 102 can prevent contamination of the thread 80 from exposure to an ambient environment, or from a person touching the thread 80. For example, contamination or damage to the thread can be prevented when the cover member 102 is coupled to the base 104 and extends over an outer surface of the thread 80. Damage to the thread can be avoided by preventing inadvertent touching or engagement of the thread 80. The cover member 102 and base 104 can prevent moisture from the patient's skin or tissue (e.g., dermis, epidermis, and/or subcutaneous tissue) from moving through or around the cover member to the thread 80. The cover member 102 can seal the inner cavity from ingress of fluid toward the thread 80 to avoid hydration of the thread 80 during insertion of the cover member 102 into the patient.

To restrict and permit movement of the cover member 102 relative to the base 104, the insertion device 100 can comprise a moveable release member 120, as illustrated in FIGS. 3-6. The moveable release member 120 can engage the cover member 102 to restrict or permit separation of the cover member 102 from the base 104. The moveable release member 120 can comprise a button 122, as illustrated in FIG. 4, to be actuated by a physician to restrict or permit movement of the cover member 102 relative to the base 104. The button 122 can be positioned to permit a physician to hold the insertion device 100 and actuate the button 122 with a single hand. The button 122 can be configured to be depressed to be actuated.

A proximal portion of cover member 102 can be positioned within the base 104 and engaged by the moveable release member 120, and a distal portion extends from the base 104. In a first configuration, a portion of the moveable release member 120 can engage the cover member 102 to restrict separation of the cover member 102 from the base 104. In a second configuration, the moveable release member 120 can be moved to permit the cover member 102 to be separated from the base 104. In some embodiments, the moveable release member 120 can be configured, in a first configuration, to permit the cover member 102 to be separated from the base 104. In a second configuration, the moveable release member 120 can be moved to restrict separation of the cover member 102 from the base 104.

The moveable release member 120 can comprise an obstruction member 130 that extends from the button 122 to restrict or permit movement of the cover member 102. The moveable release member 120 can restrict movement of the cover member 102 along a cover member axis that extends through the longitudinal length of the cover member.

The obstruction member 130 can have a proximal portion coupled to the button 122 and a distal portion that extends from the button 122 into the base 104, as illustrated in FIG. 4. Referring to the cross-sectional detail view of FIGS. 5 and 6, the distal portion of the obstruction member 130 can extend into a cavity of the base 104 configured to receive the proximal portion of the cover member 102. A first segment 132 of the obstruction member 130 can comprise an outer surface having a cross-sectional width that tapers away from a distal end of the obstruction member 130. A second segment 134 of the obstruction member 130, between the first segment 132 and a distal end, can comprise an outer surface having a cross-sectional width that tapers toward the distal portion. A portion of the first segment 132 can have a cross-sectional width that is less than a cross-sectional width of a portion of the second segment 134, such that the second segment 134 of the obstruction member 130 can obstruct movement of the cover member 102, and the first segment 132 can permit movement of the obstruction member 130. The first segment 132 can comprise a groove 136 that extends along a length of the obstruction member 130.

The insertion device 100 can be configured with the movable release member 120 that is movable between a first configuration and a second configuration. In the first configuration, as illustrated in FIG. 5, the movable release member 120 can be positioned in the base 104 with the second segment 134 aligned with respect to the cover member 102. The outer surface of the second segment 134 can be engaged against an outer surface of the cover member 102 to urge the cover member 102 against a surface of the base 104. Movement of the cover member 102 relative to the base 104 is restricted when the cover member 102 is urged against the base 104. In the second configuration, illustrated in FIG. 6, the obstruction member 130 can be moved or actuated so that the first segment 132 is aligned with respect to the cover member 102. The reduced cross-sectional width of the first segment 132, relative to the second segment 134, can permit movement of the cover member 102 relative to the base 104. The interference or friction engagement between the release member 120 and the cover member 102 can permit the cover member 102 to be selectively engaged until the interference or friction engagement is released by moving the release member 120. In some embodiments, the release member can be biased toward the first configuration by a biasing mechanism, such as a spring. Further, some embodiments can incorporate the engagement mechanisms disclosed in FIGS. 8-11 of U.S. patent application Ser. No. 15/414,306, filed on the same day as the present Application, the entirety of which is incorporated herein by reference.

Referring to FIG. 7, the cavity can comprise an enclosure 110 extending proximally from the first or second portion toward the proximal portion of the base 104. The enclosure 110 can extend proximally from the moveable release member 120 and house at least a portion of the thread 80 and the cover member 102 therewithin. The enclosure 110 can have a cross-section profile size that is greater than a diameter or cross-sectional profile of the thread 80 to permit a portion of the thread to move within the enclosure 110. As such, a portion of the thread 80 can gather or be retained within the enclosure 110. A proximal portion of the thread 80 can be positioned within the enclosure 110 with a distal portion of the thread 80 extending through the first portion 106 of the cavity. The thread can extend between any of the enclosure 110, first portion 106, and the cover member 102. The thread 80 can be moved into or withdrawn from the enclosure 110. For example, a distal portion of the thread 80 can be pulled or moved, relative to the base 104, to withdraw a proximal portion of the thread 80 from the enclosure 110.

In the first configuration, a portion of the moveable release member 120 can be separated from an inner surface the base 104, and in the second configuration, a portion of the moveable release member 120 can engage the inner surface of the base 104 to limit movement of the moveable release member 120. A distal portion of the movable release member 120 can be separated from an inner surface of the base 104 and the first configuration, and in the second configuration, the movable release member 120 can be moved until the distal portion engages the inner surface of the base 104.

To use the insertion device 100, a proximal portion of the thread 80 can be positioned within the base 104 with the distal portion of the thread 80 extending from the base 104. The cover member 102 can be coupled to the base 104 so that the distal portion of the thread 80 can extend within the cavity of the cover member 102. As noted above, a portion of the thread 80, such as the proximal portion, can be coupled to or separated from and moveable relative to the base 104. For example, in some embodiments, a portion of the thread 80 can be adhered to the base 104. However, although the base 104 and the thread 80 can be coupled together, some embodiments can provide advantages by permitting the thread 80 to be free from the base 104.

Figure 8:
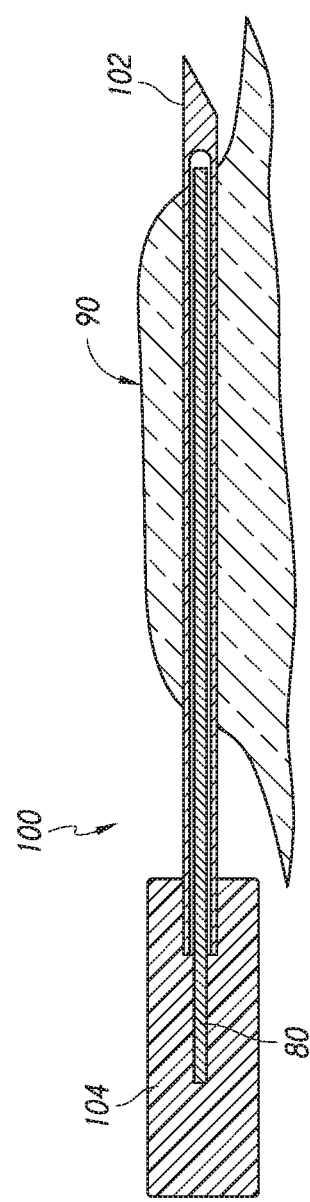
FIGS. 8-10 are cross-sectional side views of an insertion device, according to some embodiments.

In use, the insertion device 100 can be directed toward a patient's skin so that the tapered distal portion of the cover member 102 pierces the skin and permits further movement of the insertion device 100 into the patient. An opening can be created through the patient's skin by a separate device. The insertion device 100 can be moved into the patient until a portion of the cover member 102 exits through a second portion of the patient's skin 90, as illustrated in FIG. 8. The insertion device 100 can be moved relative to a longitudinal and transverse axis of the device to position the thread 80 at a specific location. In some methods, movement of the insertion device 100 can comprise inserting, retracting, pitching, rolling, and/or yawing relative to the longitudinal and transverse axis and the patient.

Figure 9:
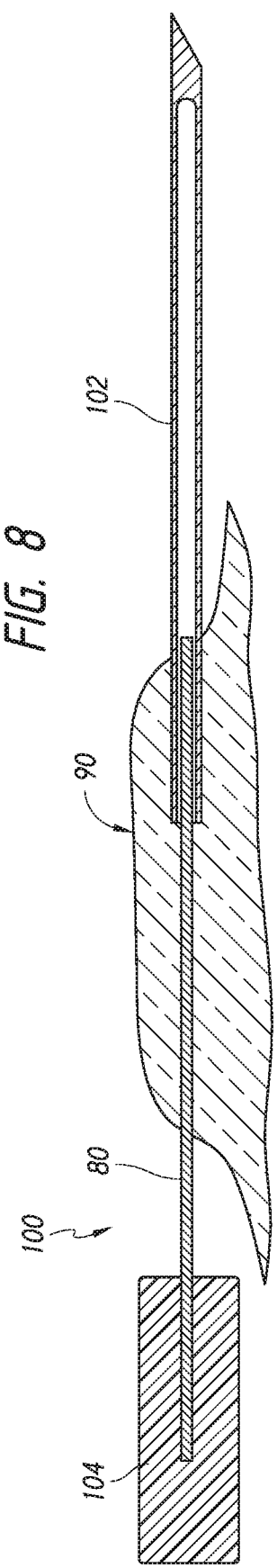

When the thread 80 is in the position where it is to be implanted, the cover member 102 can be separated from the base 104. The cover member 102 can be separated from the base 104 and withdrawn from the patient through the second portion of skin 90, as illustrated in FIG. 9. The movable release member can be actuated to permit separation of the cover member 102 from the base 104. When the cover member 102 is withdrawn, a proximal portion of the thread can remain coupled to the base 104 and a distal portion of the thread 80 exposed to the patient. The base 104 can be moved to change the orientation or position of the thread 80 within the patient. In some methods, the base 104 is retracted so that a distal portion of the thread 80 does not extend through the second portion of the skin 90.

Figure 10:
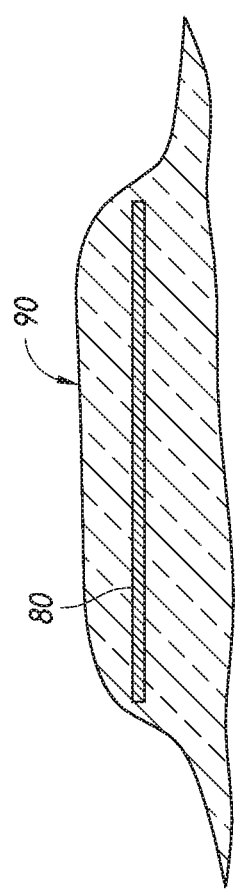

To permit the thread 80 to remain with the patient, the thread 80 and base 104 are separated, as illustrated in FIG. 10. To separate the thread 80, the proximal and distal portions of the thread 80 can be separated. To separate the proximal and distal portions of the thread 80, the base 104 and proximal portion of the thread 80 can be moved relative to the distal portion of the thread 80. The base can be moved by twisting base 104 and proximal portion of the thread 80 relative to the distal portion. The proximal and distal portions of the thread 80 can be separated by cutting the thread 80, moving a portion of the base 104 to release the thread, and/or moving the base and thread in opposing directions.

In some embodiments, the thread 80 is not coupled to the base 104. In using such embodiments, when the thread 80 is in the position where it is to be implanted, the base 104 can be separated from the cover member 102 without proximally withdrawing the thread 80 (i.e., the thread 80 remains in place in the cover member 102). The movable release member can be actuated to permit separation of the base 104 from the cover member 102. When the base 104 is separated, the cover member 102 and thread 80 within the cover member 102, remain within the patient. To release the thread 80 subcutaneously within the patient, the physician can grasp a proximal portion of the thread 80 and, while holding the thread 80, pull the cover member 102 through the exit point or second portion of the skin 90. Thus, the thread 80 can be retained in a desired subcutaneous position when the base 104 and the cover member 102 are removed.

Referring now to FIGS. 11-17, some embodiments of the insertion device can be configured to comprise a cover member that can move or change from a rigid insertion configuration to a flexible state in situ that allows the cover member to expose the thread and facilitate removal of the cover member from the skin. For example, the cover member can comprise a material that can be activated from the insertion configuration in situ, such as by softening when hydrated in situ, by being electrically activated by a pulse of electricity, and/or by being exposed to heat, such as a heat-scalable, expandable, and/or shape memory material that moves from the insertion configuration after a period of time of being positioned in situ within the patient. For example, the cover member can change shape when exposed to a temperature of between about 80° F. and about 96° F. In some embodiments, the cover member can change shape when exposed to a temperature of at least 85° F. Further, in some embodiments, the cover member can change shape when exposed a temperature of at least 90° F. Such temperature ranges can be reached when the cover member is implanted subcutaneously within a patient.

For example, FIG. 11 illustrates an insertion device 250 that can comprise a moveable member 252, a base 254, and a HA thread 80. A portion of the moveable member 252 can comprise a moveable material, e.g., a shape memory material. The moveable member 252 can move to prevent contamination or damage to the thread, and to expose or release the thread. The moveable member 252 can function to provide both a covering and a support for the thread, combining the cover member and the support member features of other embodiments.

FIGS. 12 and 13 illustrate the insertion device 250 in an insertion configuration, with the movable member 252 and a rigid state, which allows the physician to advance the movable member 252 through the skin. Next, FIGS. 14 and 15 illustrate the insertion device 250 after the movable member 252 has been activated from the insertion configuration. Finally, FIGS. 16 and 17 illustrate the insertion device 250 being removed from the patient with the movable member 252 in an expanded state.

Referring again to FIG. 11, the movable member 252 can comprise a shaft, a rod, and/or a plate having a longitudinal axis that extends between a proximal portion and a distal portion. The proximal portion of the movable member 252 can be coupled to the base 254. In some embodiments, the movable member 252 can be formed unitarily with the base 254 and secured thereto such that movement of the movable base 254 causes movement of the movable member 252. However, the movable member 252 can also be removably coupled to or detachable from the base 254. The distal portion of the movable member 252 can be configured to retain a portion of a thread 80 within an enclosure, cavity, or channel 256.

In some embodiments, the movable member 252 can comprise a sheet of material that can have be rigid prior to and during the injection procedure, but become flexible, shrink, and/or unfurl or expand from a cylindrical shape within a period of time after being subcutaneously injected into the patient. The sheet of material can comprise laterally extending portions or wings 260 that curl into the cylindrical shape to house a portion of a thread 80. The wings 260 can thereby create the enclosure 256 that encloses the thread 80 therewithin. The movable member 252 can at least partially or fully enclose the thread 80 within the enclosure 256 formed by the wings 260. The thread 80 can be positioned along the movable member 252 so that a proximal portion of the thread 80 is adjacent to the base 254, and a distal portion of the thread 80 is within the enclosure 256 of the movable member 252, as illustrated in FIG. 11. In some embodiments, the proximal portion of the thread 80 can be coupled to the base 254.

The distal portion of the movable member 252 can comprise a closed distal portion to close the enclosure 256. For example, the distal portion of the movable member 252 can be collapsed to form a pointed tip in order to facilitate piercing and passage of the device 250 through the skin 90. In some embodiments, the movable member 252 can comprise an alloy, such as an alloy of nickel and titanium (e.g., nitinol).

FIGS. 12 and 13 illustrates the insertion device 250 in the insertion configuration. As shown, the wings 260 can extend from the distal portion of the movable member 252 to create the enclosure 256 that extends at least partially along a longitudinal length of the movable member 252. In the insertion configuration, the movable member 252 can have a tubular cross-sectional profile in which distal portions 262 of the wings 260 are positioned adjacent to each other. The cross-sectional profile can comprise a shape that is circular, square, rectangular, L-shaped, and/or U-shaped.

In the insertion configuration, the insertion device 250 can enclose a portion of the thread 80. The wings 260 can surround a circumference of the thread and extend along a longitudinal length of the thread 80. The wings 260 can extend along a portion of the longitudinal length of the thread 80, e.g., the proximal or distal portions, or the entire length of the thread 80, e.g., the proximal and distal portions.

In FIGS. 14 and 15, the insertion device 250 is shown as the movable member 252 begins to be actuated and become flexible, expand, or laterally shrink. Although it is not required, the moveable member 252 can expand from the insertion configuration. Further, the distal portions 262 of the wings 260 can laterally shrink and retract toward the movable member 252 to open the enclosure in the second configuration. Further, the wings 260 can soften while retaining sufficient tensile strength to permit the wings 260 and the movable member 252 to be retracted from within the skin of the patient. Thus, in some embodiments, such as that illustrated in FIGS. 14-17, the wings 260 of the moveable member 252 can begin to move away from the thread 80, thereby opening the enclosure 256. The wings 260 can move so that the distal portions 262 of the wings 260 unfold away from the thread to open the enclosure and create a channel or planar surface. As the wings 260 separate from each other, the thread 80 becomes exposed from within the enclosure 256 of the moveable member 252, as illustrated in FIG. 15. In some embodiments, the longitudinal length of the moveable member 252 can remain constant along the distal portion of the thread when the movable member 252 is in the insertion configuration and as it is actuated and/or expands from the insertion configuration.

The movable member 252 can comprise a shape memory material configured to move once activated or deactivated. The distal portion of the movable member 252 can comprise the shape memory material. The shape memory material can be activated or deactivated by heating the cover member. In some examples, electricity can be applied to the cover member for resistive heating, or the cover member can be exposed to the patient's body heat during insertion of the device into the patient. Accordingly, the movable member 252 can comprise a material that can be activated from the insertion configuration in situ, such as by softening when hydrated in situ, by being electrically activated by a pulse of electricity, and/or by being exposed to heat, such as a heat-scalable, expandable, and/or shape memory material that moves from the insertion configuration after a period of time (e.g., between at least about 10 seconds to about 1 minute) of being positioned in situ within the patient.

Referring to FIGS. 16 and 17, after the moveable member 252 is positioned within the patient at a desired position and the moveable member 252 is activated, the thread 80 can be exposed and begin to be hydrated in situ, thus swelling and engaging with surrounding tissue. In some embodiments in which the thread 80 is attached to the base 254, in order to separate the thread 80 from the insertion device, the proximal portion of the thread can be severed from the base 254. For example, a release member of the base 254 can be actuated to permit the thread to separate from the insertion device 250. Once a suitable amount of time has passed (e.g., between at least about 10 seconds to about 1 minute) in order to permit hydration of the thread 80, the insertion device 250 can be retracted from the patient. As the moveable member 252 is withdrawn, all remaining circumference or outer surface of the thread 80 can be exposed in situ. Any portion of the thread 80 that remains extending through the surface of the patient's skin can be separated or cut so that the remaining portion is entirely within the patient's skin.

Further Considerations

In some embodiments, any of the clauses herein may depend from any one of the independent clauses or any one of the dependent clauses. In one aspect, any of the clauses (e.g., dependent or independent clauses) may be combined with any other one or more clauses (e.g., dependent or independent clauses). In one aspect, a claim may include some or all of the words (e.g., steps, operations, means or components) recited in a clause, a sentence, a phrase or a paragraph. In one aspect, a claim may include some or all of the words recited in one or more clauses, sentences, phrases or paragraphs. In one aspect, some of the words in each of the clauses, sentences, phrases or paragraphs may be removed. In one aspect, additional words or elements may be added to a clause, a sentence, a phrase or a paragraph. In one aspect, the subject technology may be implemented without utilizing some of the components, elements, functions or operations described herein. In one aspect, the subject technology may be implemented utilizing additional components, elements, functions or operations.

The subject technology is illustrated, for example, according to various aspects described below. Various examples of aspects of the subject technology are described as numbered clauses (1, 2, 3, etc.) for convenience. These are provided as examples and do not limit the subject technology. It is noted that any of the dependent clauses may be combined in any combination, and placed into a respective independent clause, e.g., clause 1 or clause 5. The other clauses can be presented in a similar manner.

Clause 1. A thread insertion assembly comprising: a cover member comprising a proximal portion, a closed distal portion, and an inner cavity extending from the proximal portion toward the closed distal portion; a base removably coupled to the proximal portion of the cover member; and a thread positioned within the inner cavity and extending from the base toward the closed distal portion; wherein the cover member is insertable into a patient and separable from the base to expose the thread.

Clause 2. The thread insertion assembly of Clause 1, wherein the thread comprises a proximal portion and a distal portion, the proximal portion of the thread being coupled to the base.

Clause 3. The thread insertion assembly of any one of the preceding Clauses, wherein the cover member comprises a rigid tubular member.

Clause 4. The thread insertion assembly of any one of the preceding Clauses, wherein the cover member comprises a metal material.

Clause 5. The thread insertion assembly of any one of the preceding Clauses, wherein the base comprises a moveable release member engaged with the cover member, wherein movement of the release member permits the cover member to be separated from the base.

Clause 6. The thread insertion assembly of Clause 5, wherein in a first configuration, the cover member is engaged between the moveable release member and the base, and in a second configuration, the cover member is released by movement of the moveable release member.

Clause 7. The thread insertion assembly of Clause 6, wherein the base comprises a cavity, and the moveable release member is positioned within a cavity of the base such that in the first configuration, a distal portion of the moveable release member is separated from the cavity, and in the second configuration, the distal portion engages the cavity.

Clause 8. The thread insertion assembly of Clause 5, wherein the moveable release member comprises a first portion having a first cross-sectional width, and a second portion having a second cross-sectional width that is greater than the first cross-sectional width.

Clause 9. The thread insertion assembly of Clause 8, wherein the first portion comprises an outer surface comprising a groove extending along a longitudinal length of the moveable release member.

Clause 10. The thread insertion assembly of any one of the preceding Clauses, wherein at least a portion of the cover member is less flexible relative to the thread.

Clause 11. The thread insertion assembly of any one of the preceding Clauses, wherein the cover member comprises a tubular member having a closed distal portion with a beveled outer surface.

Clause 12. The thread insertion assembly of any one of the preceding Clauses, wherein the proximal portion of the cover member extends into the base.

Clause 13. The thread insertion assembly of any one of the preceding Clauses, wherein the cover member comprises a tubular member.

Clause 14. The thread insertion assembly of any one of the preceding Clauses, wherein the cover member comprises a hypodermic tube.

Clause 15. The thread insertion assembly of any one of the preceding Clauses, wherein the cover member seals the inner cavity from ingress of fluid toward the thread to avoid hydration of the thread during insertion of the cover member into the patient.

Clause 16. The thread insertion assembly of any one of the preceding Clauses, wherein the distal portion comprises a bevel.

Clause 17. The thread insertion assembly of any one of the preceding Clauses, wherein the cover member comprises stainless steel.

Clause 18. The thread insertion assembly of any one of the preceding Clauses, wherein the thread comprises a filament.

Clause 19. The thread insertion assembly of any one of the preceding Clauses, wherein the moveable release member comprises a tapered cross-sectional width.

Clause 20. A method of inserting a thread comprising: inserting a distal portion of a cover member into a patient, wherein the cover member comprises a proximal portion, a closed distal portion, and an inner cavity extending from the proximal portion toward the closed distal portion, and wherein the proximal portion of the cover member is coupled to a base, and a thread is positioned within the inner cavity between the base and the distal portion; and separating the cover member relative to the base to expose the thread.

Clause 21. The method of Clause 20, comprising separating the thread from the base.

Clause 22. The method of Clause 21, wherein separating the cover member comprises actuating a moveable release member engaged with the cover member, wherein movement of the release member permits the cover member to be separated from the base.

Clause 23. The method of Clause 22, wherein actuating a moveable release member comprises depressing a button.

Clause 24. The method of any one of the Clauses 20 to 23, wherein inserting a distal portion of a cover member into a patient comprises inserting a distal portion of a cover member into a patient through at a first point, and separating a proximal portion of the cover member comprises moving the cover member to exit the patient at a second point, different than the first point.

Clause 25. The method of any one of the Clauses 20 to 24, wherein separating a proximal portion of the cover member comprises moving the cover member distally to the base.

Clause 26. The method of any one of the Clauses 20 to 25, wherein inserting a distal portion of a cover member into a patient comprises inserting the distal end of the cover member into the skin.

Clause 27. A method of inserting a thread comprising: inserting a distal portion of a moveable member into a patient, in a first configuration, wherein the moveable member extends along distal portion of a thread and surrounds a circumference of the thread; and unfolding the moveable member away from the thread in a second configuration to expose the thread.

Clause 28. The method of Clause 27, comprising retracting the distal portion of the moveable member from the patient.

Clause 29. The method of Clause 28, comprising retracting the moveable member in the first configuration.

Clause 30. The method of Clause 28, comprising retracting the moveable member in the second configuration.

Clause 31. The method of any one of Clauses 27 to 30, wherein unfolding the moveable member comprises exposing the moveable member to a temperature of between about 80° F. to about 96° F.

Clause 32. The method of any one of the Clauses 27 to 31, wherein unfolding the moveable member comprises exposing the moveable member to a temperature of at least 85° F.

Clause 33. The method of any one of the Clauses 27 to 32, wherein unfolding the moveable member comprises exposing the moveable member to a temperature of at least 90° F.

Clause 34. A thread insertion assembly comprising: a moveable member comprising a proximal portion and a distal portion that extends along a portion of a thread, wherein the distal portion of the moveable member comprises laterally extending portions that surround a circumference of the thread in a first configuration, and circumferentially unfolds away from the thread in a second configuration to expose the thread.

Clause 35. The thread insertion assembly of Clause 32, wherein the distal portion of the moveable member extends along the distal portion of the thread.

Clause 36. The thread insertion assembly of Clause 33, wherein a longitudinal length of the moveable member, along the distal portion of the thread, remains constant in the first and second configurations.

Clause 37. The thread insertion assembly of any one of Clauses 32 to 34, wherein the distal portion of the moveable member defines a cavity in the first configuration.

Clause 38. The thread insertion assembly of Clause 35, wherein the cavity comprises a closed distal portion enclosing the cavity.

Clause 39. The thread insertion assembly of any one of Clauses 32 to 36, comprising a base coupled to the proximal portion of the moveable member.

Clause 40. The thread insertion assembly of any one of Clauses 32 to 37, wherein the laterally extending portions expand in the second configuration.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

What is claimed is:

1. A method of inserting a thread comprising:
   piercing a patient's skin with a closed distal portion of a cover member having a tapered outer surface, wherein the cover member comprises a proximal portion, the closed distal portion, and an inner cavity extending from the proximal portion toward the closed distal portion, and wherein the proximal portion of the cover member is coupled to and extends into a base having a cavity and a moveable release member, and a thread comprising proximal and distal portions, the thread extending from the base toward the closed distal portion of the cover member, wherein the distal portion of the thread is positioned within the inner cavity of the cover member;
   inserting the cover member into the patient; and
   moving the moveable release member to separate the cover member from the base and the thread to expose the distal portion of the thread in situ.

2. The method of claim 1, comprising separating the thread from the base.

3. The method of claim 2, wherein separating the cover member comprises moving the moveable release member relative to the base.

4. The method of claim 3, wherein moving the moveable release member comprises depressing a button.

5. The method of claim 1, wherein inserting the cover member into a patient comprises inserting the distal portion of the cover member into the patient through a first point in the skin.

6. The method of claim 5, further comprising removing the cover member through a second point in the skin, different than the first point.

7. The method of claim 1, wherein separating the cover member comprises moving the cover member distally relative to the base.

8. The method of claim 1, wherein inserting a distal portion of a cover member into a patient comprises inserting the distal end of the cover member into the skin.

9. The method of claim 1, wherein the proximal portion of the cover member extends into the cavity of the base.

10. A thread insertion assembly comprising:
    a cover member comprising a proximal portion, a closed distal portion, and an inner cavity extending from the proximal portion toward the closed distal portion, the distal portion having a tapered outer surface configured to pierce a patient's skin;

a base comprising a cavity and a moveable release member, wherein a portion of the cover member extends into the cavity of the base; and a thread comprising proximal and distal portions, the thread extending from the base toward the closed distal portion of the cover member, wherein the distal portion of the thread is positioned within the inner cavity of the cover member;

wherein the moveable release member is moveable to permit separation of the cover member from the base and the thread to expose the distal portion of the thread in situ.

11. The thread insertion assembly of claim 10, further comprising a first configuration wherein the moveable release member is engaged against the cover member to resist separation of the cover member from the base.

12. The thread insertion assembly of claim 11, wherein in the first configuration, the cover member is engaged between the moveable release member and the base.

13. The thread insertion assembly of claim 11, further comprising a second configuration wherein a portion of the moveable release member is moved away from the cover member to permit separation of the cover member from the base.

14. The thread insertion assembly of claim 10, wherein a portion of the moveable release member extends into the cavity of the base.

15. The thread insertion assembly of claim 10, wherein a portion of the thread extends through the cavity.

16. The thread insertion assembly of claim 10, wherein the cover member comprises a rigid tubular member.

17. The thread insertion assembly of claim 10, wherein the cover member comprises a metal material.

18. The thread insertion assembly of claim 10, wherein the thread comprises a proximal portion and a distal portion, the proximal portion of the thread being coupled to the base.

19. The thread insertion assembly of claim 10, wherein, when the cover member extends into the cavity of the base, the cover member is configured to resist ingress of fluid into the cavity to avoid hydration of the thread during insertion of the cover member into the patient.

20. The thread insertion assembly of claim 10, wherein the thread is a dermal filler thread.

21. The thread insertion assembly of claim 10, wherein the thread comprises hyaluronic acid.

* * * * *